United States Patent
Spincemaille et al.

(10) Patent No.: US 8,200,311 B2
(45) Date of Patent: Jun. 12, 2012

(54) CARDIAC MOTION ARTIFACT SUPPRESSION USING ECG ORDERING

(75) Inventors: Pascal Spincemaille, New York, NY (US); Yi Wang, New York, NY (US); Martin R. Prince, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 940 days.

(21) Appl. No.: 11/737,812

(22) Filed: Apr. 20, 2007

(65) Prior Publication Data

US 2007/0287907 A1   Dec. 13, 2007

Related U.S. Application Data

(60) Provisional application No. 60/745,298, filed on Apr. 21, 2006.

(51) Int. Cl.
*A61B 5/055* (2006.01)

(52) U.S. Cl. .......................... 600/413; 382/128

(58) Field of Classification Search ................. 600/413, 600/428, 509; 382/128
See application file for complete search history.

(56) References Cited

U.S. PATENT DOCUMENTS

| | | | |
|---|---|---|---|
| 5,417,213 A | 5/1995 | Prince | |
| 5,553,619 A | 9/1996 | Prince | |
| 5,579,767 A | 12/1996 | Prince | |
| 5,590,654 A | 1/1997 | Prince | |
| 5,746,208 A | 5/1998 | Prince | |
| 5,762,065 A | 6/1998 | Prince | |
| 5,792,056 A | 8/1998 | Prince | |
| 5,799,649 A | 9/1998 | Prince | |
| 5,827,187 A | 10/1998 | Wang et al. | |
| 5,924,987 A | 7/1999 | Meaney et al. | |
| 5,928,148 A | 7/1999 | Wang et al. | |
| 6,167,293 A | 12/2000 | Cheneveet et al. | |
| 6,198,959 B1 | 3/2001 | Wang | |
| 6,230,040 B1 * | 5/2001 | Wang et al. | 600/415 |
| 6,230,041 B1 | 5/2001 | Prince | |
| 6,240,311 B1 | 5/2001 | Prince | |
| 6,243,600 B1 | 6/2001 | Prince | |
| 6,278,892 B1 | 8/2001 | Prince | |
| 6,311,085 B1 | 10/2001 | Prince | |
| 6,463,318 B2 | 10/2002 | Prince | |
| 6,564,085 B2 | 5/2003 | Meaney et al. | |
| 6,662,038 B2 | 12/2003 | Prince | |
| 6,741,881 B2 | 5/2004 | Prince | |
| 6,754,521 B2 | 6/2004 | Prince | |
| 6,791,323 B2 | 9/2004 | Wang et al. | |

(Continued)

OTHER PUBLICATIONS

Du Yiping. Prospective navigator gating with a dual acceptance window technique to reduce respiratory motion artifacts in 3D MR coronary angiography. The International Journal of Cardiovascular Imaging. 19:157-162. 2003.*

(Continued)

*Primary Examiner* — Parikha Mehta

(57) ABSTRACT

Described is a robust electrocardiogram (ECG) ordering technique of k-space for breath hold contrast enhanced magnetic resonance angiography (CE-MRA) that acquires the central part of k-space in a motion-free portion of diastole and fills in from the periphery of k-space at all other times. To make maximal use of the contrast enhancement, data is acquired continuously even when the ECG signal is lost. The ECG signal is monitored in real time. The ECG ordering technique allows a flexible acquisition matrix and is robust against ECG signal imperfections. The ECG ordering technique allows thoracic and pulmonary magnetic resonance angiography with a higher resolution when compared to the conventional gated sequence.

17 Claims, 10 Drawing Sheets

U.S. PATENT DOCUMENTS

| | | | |
|---|---|---|---|
| 6,879,853 B2 | 4/2005 | Meaney et al. |
| 6,889,072 B2 | 5/2005 | Prince |
| 6,937,883 B2 | 8/2005 | Prince |
| 7,003,343 B2 | 2/2006 | Watts et al. |
| 7,110,806 B2 | 9/2006 | Prince |
| 7,313,428 B2 | 12/2007 | Meaney et al. |
| 7,545,967 B1 | 6/2009 | Prince et al. |
| 7,680,527 B2 | 3/2010 | Prince |
| 7,689,267 B2 | 3/2010 | Prince |
| 7,729,741 B2 | 6/2010 | Meaney et al. |
| 7,734,078 B2 | 6/2010 | Prince et al. |
| 7,747,309 B2 | 6/2010 | Prince |
| 2001/0027265 A1 | 10/2001 | Prince |
| 2001/0034483 A1 | 10/2001 | Prince |
| 2002/0010397 A1 | 1/2002 | Prince |
| 2002/0068865 A1 | 6/2002 | Meaney et al. |
| 2003/0032877 A1 | 2/2003 | Watts et al. |
| 2003/0047083 A1 | 3/2003 | Prince |
| 2003/0117136 A1 | 6/2003 | Wang et al. |
| 2003/0135111 A1 | 7/2003 | Meaney et al. |
| 2003/0163036 A1 | 8/2003 | Prince |
| 2004/0068177 A1 | 4/2004 | Prince |
| 2004/0181147 A1 | 9/2004 | Prince |
| 2004/0210130 A1 | 10/2004 | Prince |
| 2005/0119557 A1 | 6/2005 | Meaney et al. |
| 2005/0203377 A1 | 9/2005 | Watts et al. |
| 2005/0272995 A1 | 12/2005 | Prince |
| 2006/0264741 A1 | 11/2006 | Prince |
| 2007/0287907 A1 | 12/2007 | Spincemaille et al. |
| 2008/0300480 A1 | 12/2008 | Meaney et al. |
| 2009/0245606 A1 | 10/2009 | Prince et al. |
| 2010/0174175 A1 | 7/2010 | Prince |

OTHER PUBLICATIONS

Permi Jhooti, MEng et al; Hybrid Ordered Phase Encoding (HOPE): An Improved Approach for Respiratory Artifact Reduction; Research Paper; Jul./Aug. 1998; pp. 968-980; vol. 8, No. 4; JMRI.

Thanh D. Nguyen et al; Optimization of view ordering for motion artifact suppression; Paper; 2001; pp. 951-957; Magnetic Resonance Imaging 19.

Miha Fuderer; The Information Content of MR Images; Paper; Dec. 1988; pp. 368-380vol. 7, No. 4; IEEE Transactions on Medical Imaging.

Osama Al-Kwifi et al; Pulsatile Motion Effects on 3D Magnetic Resonance Angiography: Implications for Evaluating Carotid Artery Stenoses; Paper; 2004; pp. 605-611; Magnetic Resonance in Medicine 52; Medical Imaging Research.

R. Watts et al; Recessed Elliptical-Centric View-Ordering for Contrast-Enhanced 3D MR Angiography of the Carotid Arteries; Paper; 2002; pp. 419-424; Magnetic Resonance in Medicine 48.

Yi Wang, PhD et al; Breath-Hold Three-dimensional Contrast-enhanced Coronary MR Angiography: Motion-matched k-Space Sampling for Reducing Cardiac Motion Effects; Paper; May 2000; pp. 600-607; vol. 215, No. 2: Radiology 2000, 215.

Paul F. Arpasi, MD et al.; MR Angiography of the Thoracic Aorta with an Electrocardiographically Triggered Breath-Hold Contrast-enhanced Sequence; Paper; Jan.-Feb. 2000; pp. 107-120; vol. 20, No. 1; RadioGraphics 2000, 20.

Peter Kalden et al; Assessment of Coronary Artery Bypass Grafts: Value of Different Breath-Hold MR Imaging Techniques; Paper; May 1999; pp. 1359-1364; AJR 1999, 172.

Bernd J. Wintersperger, MD et al; Cardiac Imaging; Patency of Coronary Bypass Grafts: Assessment with Breath-hold Contrast-enhanced MR Angiography—Value of a Non-Electrocardiographically Triggered Technique; Paper; Aug. 1998; pp. 345-351; vol. 208, No. 2; Radiology 1998, 208.

Thomas G. Vrachliotis et al; Contrast-Enhanced Breath-Hold MR Angiography for Evaluating Patency of Coronary Artery Bypass Grafts; Paper; Apr. 1997; pp. 1073-1080; AJR 1997, 168.

Anders Franck, MSc et al; Cardiac-gated MR Angiography of Pulsatile Flow: K-Space Strategies; Research Paper; May/Jun. 1995; pp. 297-307; vol. 5, No. 3; JMRI 1995, 5.

David Saloner et al; MRA Studies of Arterial Stenosis: Improvements by Diastolic Acquisition; Paper; 1994; pp. 196-203; MRM 31.

Katherine Selby, PhD et al; MR Angiography with a Cardiac-Phase—specific Acquisition Window; Research Paper; Nov./Dec. 1992; pp. 637-643; vol. 2, No. 6; JMRI 1992, 2.

Prince et al., "3D Contrast MR Angiography", Berlin: Springer, 2003.

Simonetti et al., "ECG-triggered breath-held gadolinium-enhanced 3D MRA of the thoracic vasculature"; *Proceedings of the International Society for Magnetic Resonance in Medicine—4th Scientific Meeting and Exhibition*, 1996, p. 703.

Wilman et al., "Improved centric phase encoding orders for three-magnetization-prepared MR angiography", *Magn. Reson. Med.*, 36: 384-392 (1996).

* cited by examiner

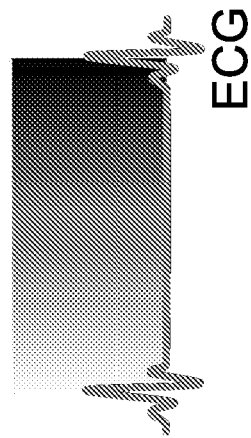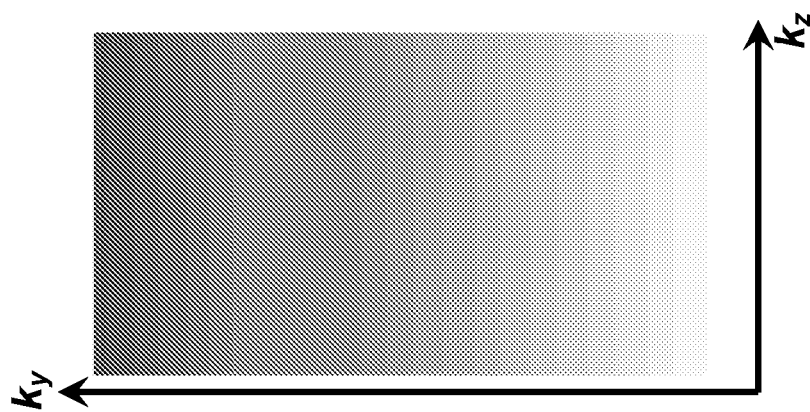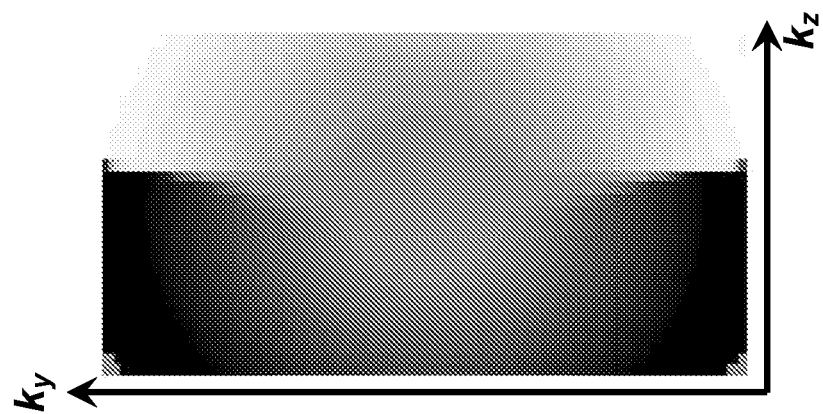
FIG. 4c
FIG. 4b
FIG. 4a

CARDIAC MOTION ARTIFACT SUPPRESSION USING ECG ORDERING

CROSS-REFERENCE TO RELATED PATENT APPLICATIONS

This patent application claims the benefit of U.S. Provisional Patent Application No. 60/745,298, filed Apr. 21, 2006, the entire disclosure of which is incorporated by reference in their entirety herein.

STATEMENT REGARDING FEDERALLY SPONSORED RESEARCH AND DEVELOPMENT

This invention was made in part with Government support under Grant Number HL060879 awarded by the National Institute of Health. The Government may have certain rights in this invention.

FIELD OF THE INVENTION

This invention generally relates to magnetic resonance imaging.

BACKGROUND OF THE INVENTION

Magnetic resonance imaging (MRI) is the method of choice for noninvasive diagnosis of soft tissue disease in humans, and has wide applications in cardiovascular diseases. For example, contrast enhanced magnetic resonance angiography (CE-MRA) allows a high resolution three dimensional depiction of the vasculature. However, in the thorax, image quality may suffer from respiratory and cardiac motion and vascular pulsation, which have the potential to cause major ghosting and blurring artifacts, thereby limiting the clinical usefulness of this technique.

Respiratory motion is counteracted by instructing patients to hold their breath. Suppressing vascular pulsation artifacts relies on ECG (electrocardiogram) triggering or gating. Restricting data acquisition to a cardiac phase specific window has been proposed for time-of-flight magnetic resonance angiography (TOF-MRA) in the lower extremities and for phase contrast magnetic resonance angiography (PC-MRA) of carotid artery disease. Systolic (maximizing inflow) or diastolic (minimizing motion) cardiac phases are used as acquisition windows when data acquisition is restricted to a cardiac phase specific window. To reduce the unavoidable lengthening of scan times, gating is restricted to views within a certain region in k-space, mostly the central part of the k-space.

The use of ECG triggering or gating has also been extended to contrast enhanced MRA. Typically, for a Cartesian acquisition matrix, all phase encodings for a fixed slice encoding are acquired in a single window within one cardiac interval using linear view ordering, which limits the possible number of phase encodings. The central slice encodings are acquired halfway through the scan. This technique has been used to evaluate coronary artery bypass graft patency and thoracic abnormalities. However, because these techniques use only a portion of the cardiac cycle, they increase scan time and do not make maximum use of the contrast bolus.

BRIEF SUMMARY

The techniques described herein provide a robust ECG ordering for contrast enhanced MRA or MRI without increasing scan time. The ECG signal (representing the cardiac cycle) is monitored in real time. The central k-space views are acquired only in the mid-diastolic rest period of the cardiac cycle. Peripheral views are acquired at any other time, allowing continuous data acquisition. This ECG ordering technique allows a flexible acquisition matrix and is robust against ECG signal imperfections.

The ECG ordering splits a k-space view table into a central view table and a peripheral view table and in one embodiment, reorders the central view table according to a recessed elliptical centric view in one embodiment. Views in the central view table are acquired during a rest period of the cardiac cycle (e.g., as indicated in an ECG signal) and each view in the peripheral view table is acquired during non-rest periods.

In one embodiment, the ECG ordering divides the peripheral view table into a first section and a second section. The first section and the second section are further divided into arches containing views that have a similar k-space radius. The acquisition of each view in the peripheral view table includes traversing an arch from the first section before the rest period and traversing an arch from the second section after the rest period.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings:

FIG. 2b is the other portion of the flowchart of FIG. 2a;

FIG. 4a is a k-space plot for ECG ordering corresponding to the k-space radius plot of FIG. 3a;

FIG. 4b is a k-space plot for sequentially ordered gating;

FIG. 4c is a plot illustrating the cardiac interval in which the k-space plots of FIGS. 4a and 4b are acquired;

FIG. 5c is an axial image derived from reformatting of sequentially ordered gated scan images of the patient of FIG. 5a;

FIG. 5d is a coronal image of the patient of FIG. 5a derived from reformatting the images of FIG. 5a;

FIG. 5e is a coronal image derived from reformatting of sequentially ordered gated scan images of the patient of FIG. 5a;

FIG. 5f is a sagital image of the patient of FIG. 5a derived from reformatting the images of FIG. 5a;

FIG. 5g is a sagital image derived from reformatting of sequentially ordered gated scan images of the patient of FIG. 5a;

FIG. 6b shows a sequentially ordered gated sequence.

Figure 1:
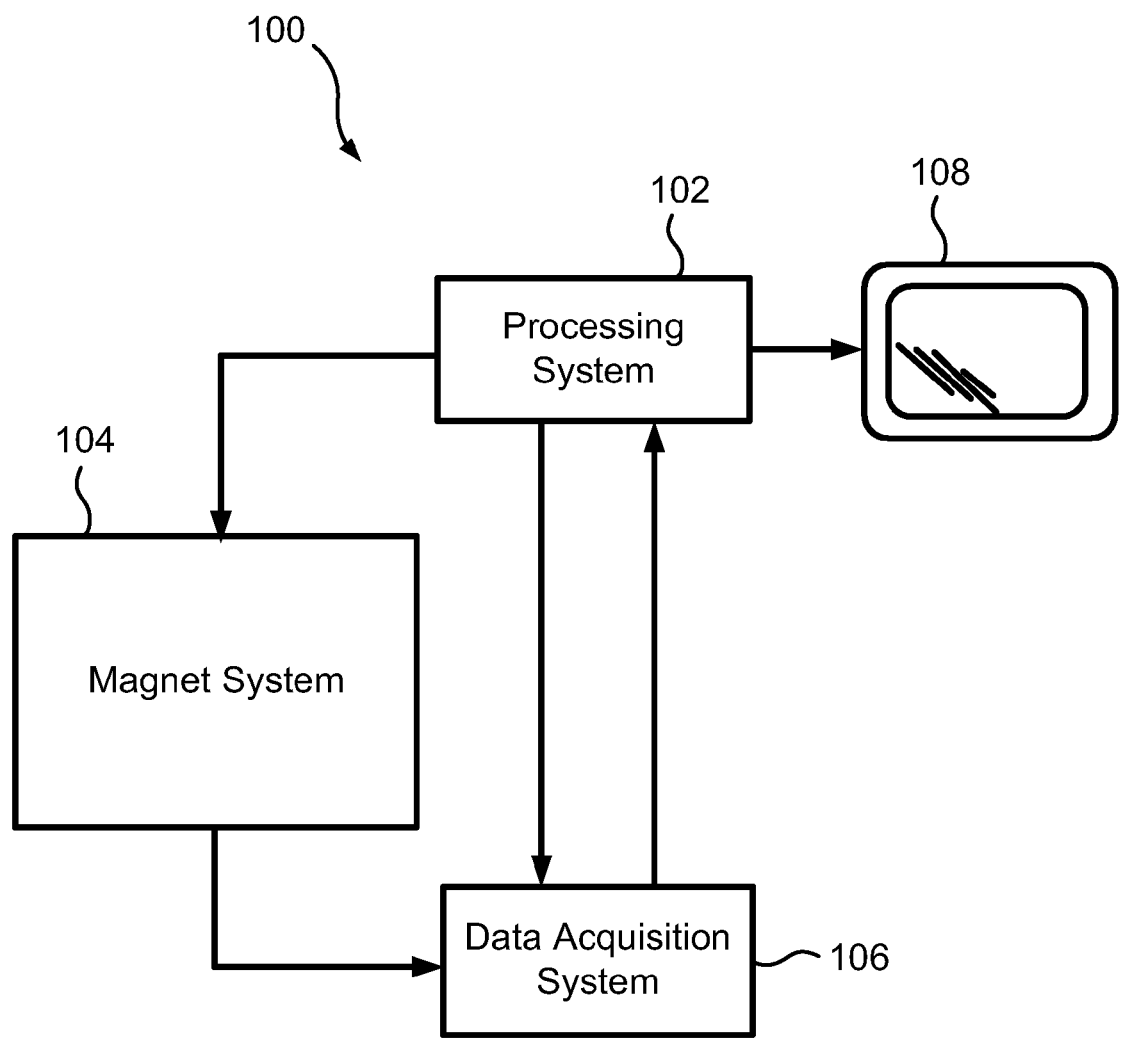
FIG. 1 is an illustration of an example of a MRI system that may be used in implementing the technology described herein.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION

Described herein is an ECG ordering technique for contrast enhanced magnetic resonance angiography (MRA) and/or imaging (MRI) that combines the advantages of fast continuous scanning, recessed elliptical-centric view ordering and cardiac phase specific acquisition of the central part of k-space. While the ECG ordering technique can be used with MRA and MRI, contrast enhanced MRA shall be used to describe the ECG ordering technique with the understanding that the technique may be used with MRI. The technique suppresses major ghosting and blurring artifacts caused by vascular pulsation and cardiac motion and does so without limiting the acquisition matrix or prolonging scan time. The ECG ordering technique allows a higher resolution MRA to be acquired within the same time frame compared to conventional techniques.

The data described herein below shows that ECG ordered contrast enhanced magnetic resonance angiography is successful in suppressing ghosting artifacts caused by vascular pulsation and in reducing blurring artifacts associated with heart motion. In this technique, image data are acquired continuously, as opposed to the sequentially ordered gated sequence. The central region of k-space is acquired only during the period of minimal motion in the cardiac cycle. ECG triggering is implemented with a fail proof algorithm that defaults to continuous elliptical centric data collection when the ECG signal is lost. This technique may be particularly important for performing high quality high resolution thoracic and cardiac MRA.

One drawback of older techniques is that data is acquired only during a fixed portion of the cardiac cycle. In the case of first pass contrast enhanced MRA where contrast material is only present for a limited amount of time, it is highly desirable to scan continuously. This is especially the case in thoracic and cardiac contrast enhanced MRA, where a breath hold is necessary. The method described herein acquires data continuously. A second difference between older techniques is that the method in one embodiment uses recessed elliptical-centric view ordering. In older techniques, all phase encodings for a given slice encoding are acquired sequentially within the same cardiac interval. In the technique taught herein, the length of the expected cardiac interval, which can be quite short for a high heart rate, does not impose any limitations on the acquisition matrix. Moreover, the recessed elliptical-centric view ordering suppresses motion artifacts and is less susceptible to timing related errors. A third difference with older techniques is the technique provides a built-in failsafe that makes sure that the sequence finishes scanning without an unreasonable extension of scan time (e.g., following a sharp increase in heart rate). It will also finish and produce images when the ECG signal is lost, a condition that causes prior ECG triggered sequences to fail, resulting in wasted scanning time and contrast material.

Figure 2A:
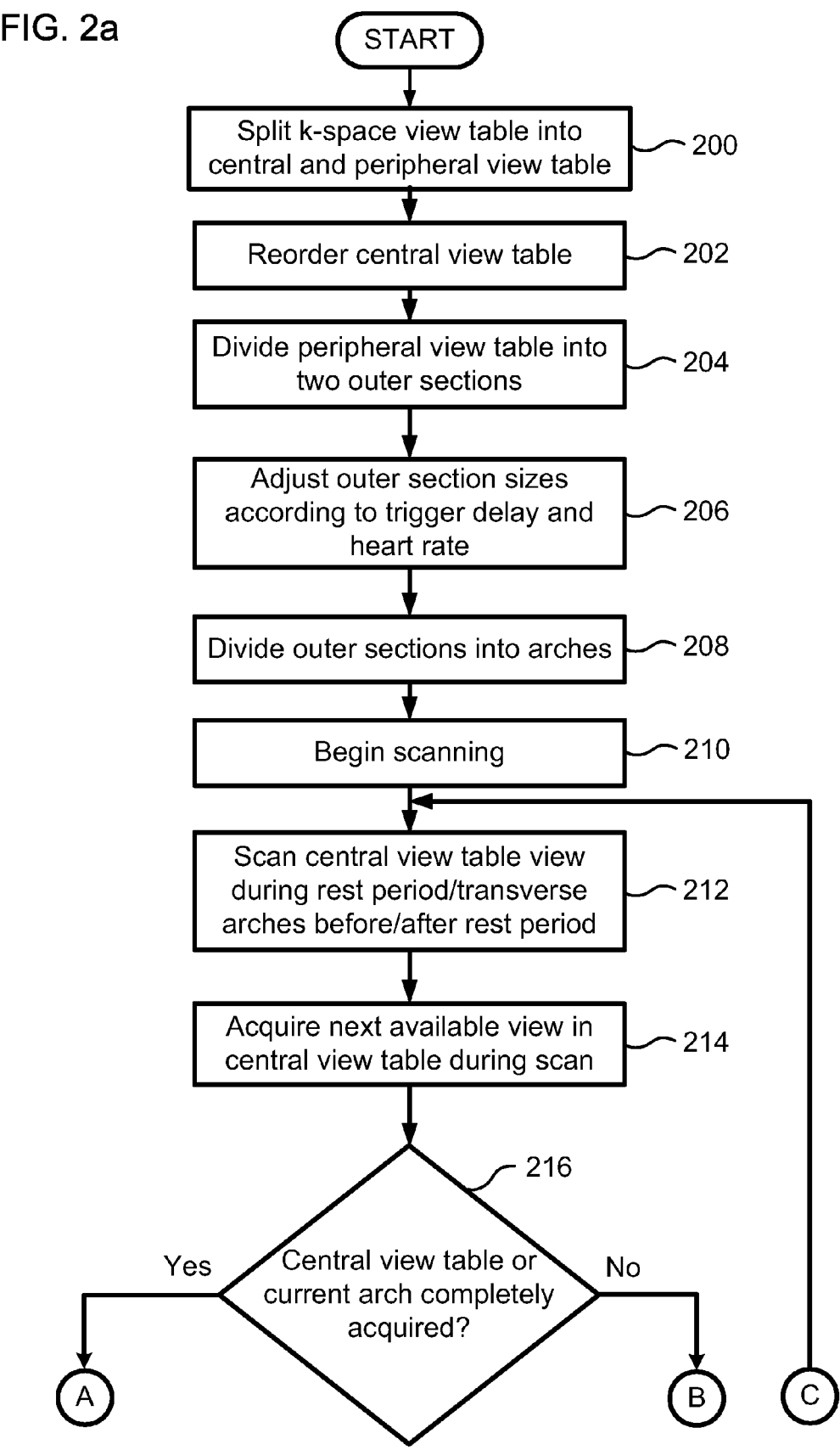
FIG. 2a is a portion of a flowchart of the steps that are taken to implement the ECG ordering technique.

In ECG ordering, the center of k-space is acquired consistently at minimal cardiac motion throughout the whole scan. However, residual motion remains in the periphery of k-space (See FIG. 2a.), degrading finer details in the image. Combined with thin slices being used, the technique described herein results in increased residual motion artifacts visible in the images compared to the sequentially ordered cardiac gated scan using thicker slices. Accordingly, in the situation of limited scan time, the ECG ordering technique forms an effective approach to reducing motion artifacts.

Compared to the product sequentially ordered cardiac gated sequence, the ECG ordered scans as described herein offer the advantage of increased volumetric coverage. It is possible to image the entire heart and the aortic root in an axial slab with relatively thin slices (e.g., 3 mm was used in the results shown below). This is especially useful for reformatting of the resulting axial views into arbitrary view planes. Moreover, total scan time is not dependent on heart rate. This sequence is also more robust against ECG signal abnormalities. For example, in one of the volunteers, ECG triggers were missed during the first five heart beats of the scan. Nevertheless, the scan finished using an elliptical centric view ordering.

Now that some of the advantages of the technique have been described, the steps of the technique shall be presented. Turning to the drawings, wherein like reference numerals refer to like elements, the technique is illustrated as being implemented in a suitable MRI data acquisition environment. Although not required, the invention will be described in the general context of computer-executable instructions, such as program modules, being executed by a personal computer. The invention may also be practiced in distributed computing environments where tasks are performed by remote processing devices that are linked through a communications network.

With reference to FIG. 1, a block diagram of an exemplary MR system 100 for implementing the invention is shown. The exemplary system includes a computer 102, a magnet system 104, a data acquisition system 106, and display 108. In general terms, the computer 102 controls the gradient and RF magnets or coils (not shown) in the magnet system 104 via amplifiers (not shown) that transmit the control signals. The computer 102 also controls the data acquisition system 106 that receives signals received by receiver coils (not shown), processes the data acquired, and outputs an image to display 108. Computer 102 typically includes a variety of computer readable media. Computer readable media can be any available media that can be accessed by computer 102 and includes both volatile and nonvolatile media, removable and non-removable media.

Figure 2B:
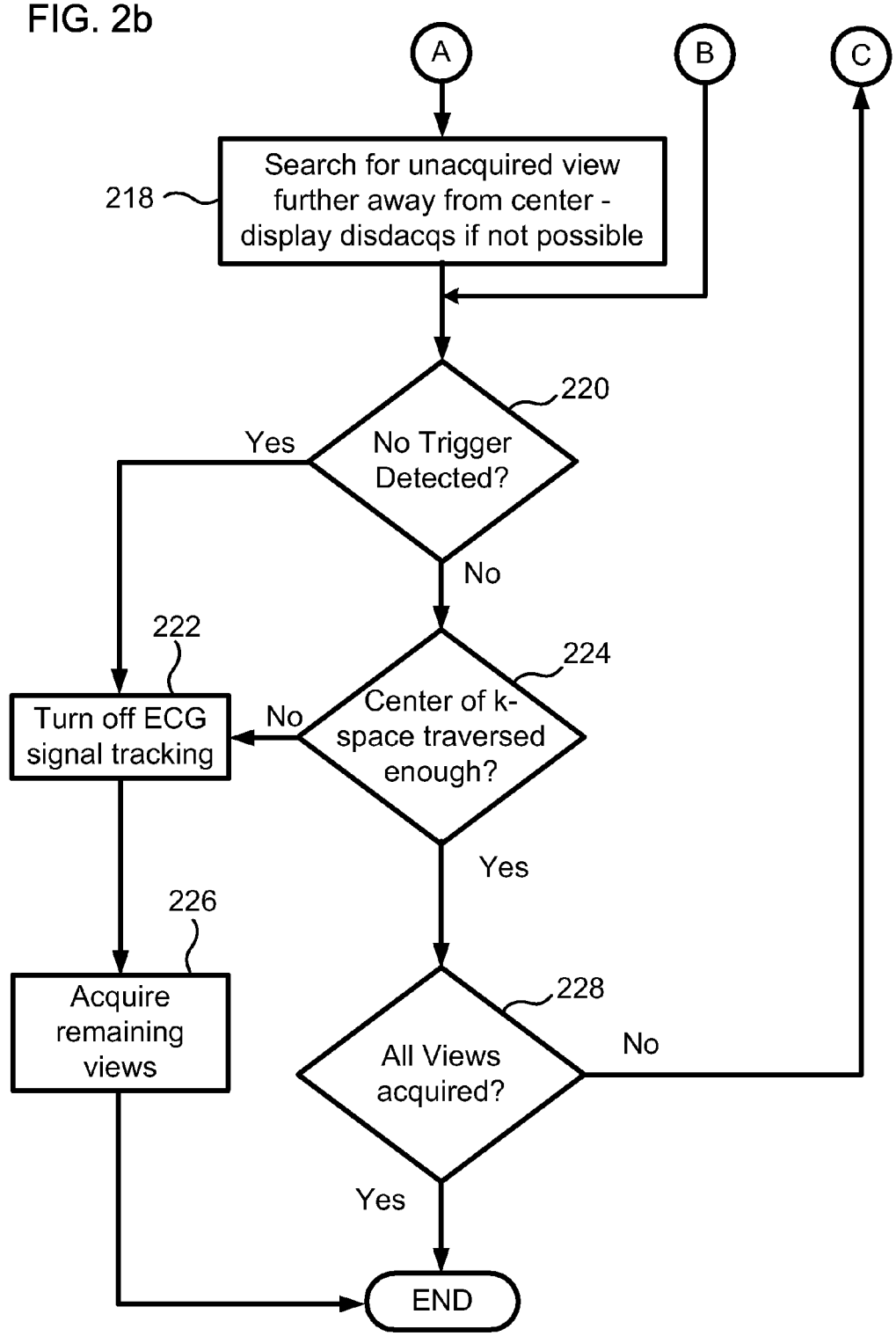
Figure 3A:
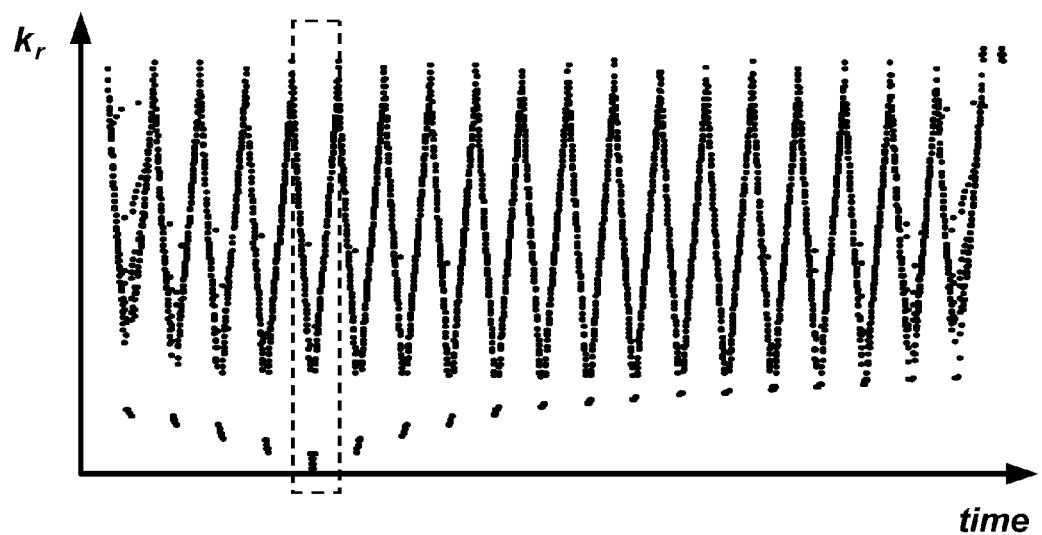
FIG. 3a is a plot of k-space radius versus time for a whole scan.
Figure 3B:
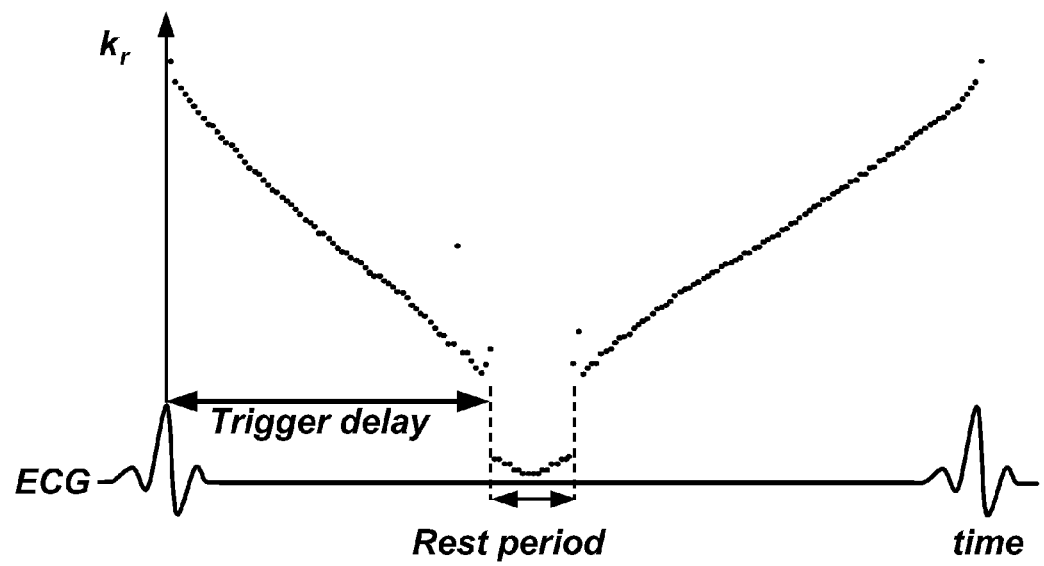
FIG. 3b is an enlarge view of a portion of the plot of FIG. 1a illustrating a trigger delay in accordance with the teachings of the invention.
Figure 3C:
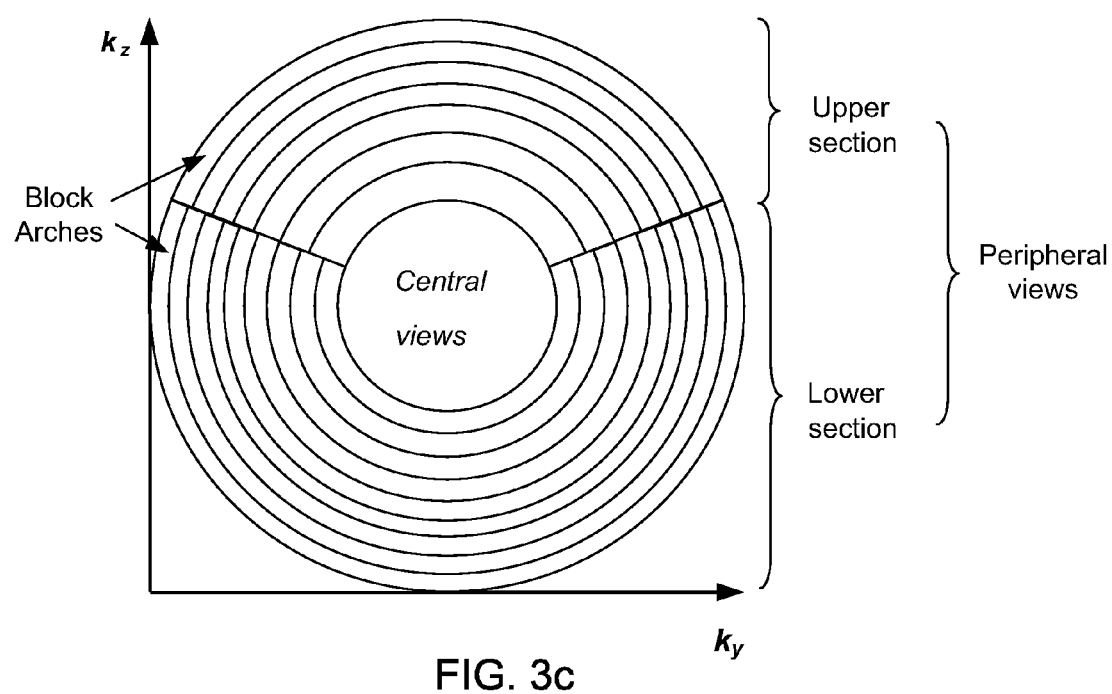
FIG. 3c is an illustration of the partitioning of k-space for ECG ordering in accordance with the teachings of the invention.

FIG. 2 shows a flow diagram of the steps taken to acquire data. Those skilled in the art will recognize that some of the steps shown being performed sequentially can be performed in parallel. The standard SPGR (spoiled gradient recalled) sequence on the scanner was modified to allow continuous monitoring of the ECG signal (which provides an indication of the cardiac cycle) without interruption of the data acquisition. The k-space view table (a table of views having N views that are to be acquired) is split into a central and a peripheral part (step 200) as illustrated in FIG. 3c. The size of the central part of k-space is equal to $N_{RP} \times N_{CI}$, where $N_{RP}$ is the number of TRs (i.e., repetition times) that fit in the rest period prescribed by the user and $N_{CI}$ is the expected number of cardiac intervals (total scan time divided by the time between two heartbeats). The central view table is reordered according to a recessed elliptical centric view with the views closest to the center of k-space shifted to a position equal to $T_{REC} \times N_{RP}$, where $T_{REC}$ is the index of the heart beat in which the absolute center of k-space was to be acquired (prescribed by the user) (step 202). FIG. 3a shows a plot of the k-space radius ($k_r = \sqrt{k_y^2 + k_z^2}$) versus time in ECG ordered MRA and FIG. 3b shows a plot of the k-space radius versus time for the fifth heart beat of FIG. 3a. The ECG ordering is determined by three parameters. These parameters are the trigger delay between the ECG trigger and the mid diastolic period of minimal cardiac motion (i.e., a rest period), the length of this period and the recess time for the recessed elliptical centric view ordering. The central k-space views are acquired within the mid-diastolic period. Note that in addition to using the sine sequence of FIGS. 3a and 3b, the rest period can also estimated empirically.

The peripheral part of k-space is divided into two sections, one containing all views with high $k_z$ and one containing views with low $k_z$ (step 204) as illustrated in FIG. 3c. During scanning, views acquired before the rest period in the cardiac cycle are taken from the first section, while those after the rest period come from the second section. The sizes of these two sections are adjusted according to the prescribed trigger delay and heart rate (step 206). Each of these outer sections is further divided into block arches (illustrated in FIG. 3c) containing $N_{CI}$ views that have a similar k-space radius (step 208). Once the above steps have been taken, scanning is done (step 210). When not scanning during the rest period, the sequence traverses the arches from the first section (outer towards inner arches) before the rest period and traverses the arches from the second section (inner back to outer arches) after the rest period (step 212). When scanning during the rest period, the sequence acquires the next available view in the central view table (step 214). This way, the sequence induces an effective recessed elliptical view order in each cardiac interval such that views closer to the center of k-space are acquired closer to the rest period. Views from the central view table are acquired only within that rest period. This edge-center-edge view order is most effective in suppressing motion artifacts. Data acquisition is never interrupted and, as a consequence, the sequence makes maximal use of the contrast present in the blood.

To deal with the inconsistent length of cardiac intervals, some precautions are used. A check is made to determine if the sequence needed to choose from a particular arch that is completely acquired (step 216). When at any given time, the sequence needed to choose from a particular arch that was completely acquired, it searches for a yet unacquired view in any of the arches (within the same outer section) further away from the k-space center. When this is not possible, disdacqs (disabled data acquisitions) are played out (step 218). This case might arise when during the scan the heart rate significantly drops. When, due to ECG signal loss or other ECG irregularities, no trigger is detected for a period equal to a predetermined number of cardiac cycles (using the heart rate at the time of scan prescription) (step 220), ECG signal tracking is turned off (step 222). In one embodiment, the predetermined number of cardiac cycles is three cardiac cycles. The sequence also detects when it did not traverse the center of k-space (step 224). This can be caused by a sharp increase or as well a sharp decrease in heart rate. When this abnormality is detected, ECG signal tracking is turned off (step 222). When ECG signal tracking is turned off, all remaining views are acquired starting from the central view table followed by inner to outer arches (step 226). If the trigger has been detected and the center of k-space has been traversed enough, the sequence determines if all views have been acquired (step 228). If all views have not been acquired, steps 212 to 228 are repeated until all remaining views are acquired, starting from the most central one and ending with the edge of k-space, in effect producing an elliptical centric view ordering. This way, the sequence finishes regardless of the quality of the ECG signal.

In order to evaluate the effectiveness of the ECG ordered sequence, it was compared to the sequentially ordered cardiac gated product pulse sequence on the scanner. This sequence acquired all phase encodings for a given slice encoding in one heartbeat and played out disdacqs until the next ECG trigger, at which point all phase encodings for the next slice encoding were acquired. Simulations of these two view orders were performed assuming (i) a constant heart rate of 60 beats per minute and (ii) a 100 ms rest period after a 400 ms delay. Gray scale plots were constructed to visualize the time within the cardiac interval when a view was acquired. Imaging parameters used for these simulations were TR/TE=6.3/1.2 ms, 192 phase encodings with 70% phase FOV and 30 slice encodings for both view orderings.

FIGS. 4a-4c provide a graphical illustration of the comparison of ECG ordering and sequentially ordered gating. FIG. 4a is a plot of k-space for ECG ordering and FIG. 4b is a plot of k-space for sequentially ordered gating. Both view orders perform a smooth mapping of k-space views onto the space of cardiac phases. The horizontal axis in FIGS. 4a and 4b represents slice ($k_z$) encoding while the vertical axis indicates phase ($k_y$) encoding. Each view is colored according to the time in the cardiac interval at which it is acquired: from white (beginning of cardiac cycle) over gray (rest period) to black (end of rest period) in accordance with the cardiac cycle in FIG. 4c, where the position of each view within the cardiac cycle is color-coded. The plot in FIG. 4a corresponds to the view order $k_r$ versus time plot in FIG. 1.

Experiments were performed on a GE Excite 1.5T scanner (GE Healthcare, Waukesha, Wis.). Before the contrast enhanced MRA, an axial cine SSFP (steady-state free precession) scan through the heart was performed to determine the ECG trigger delay and the length of the rest period. Scanning parameters were: 32 cm FOV, 65%-0.80% phase FOV, 256×160×38–46 acquisition matrix interpolated to a 512×512×76–92 image matrix, TR=3.1 ms, TE=0.8 ms, and slice thickness 3 mm. An axial slab was placed in the thorax center centered on the heart. For contrast enhancement, 15-20 cc of Magnevist (Berlex Laboratories, Wayne, N.J.) was injected immediately before scanning. The subject was instructed to hold his breath during the 18-21 seconds scan time. This scan was repeated 10 to 15 seconds later.

Six healthy volunteers and seven patients with confirmed cardiac disease were enrolled in a study. For every volunteer, two injections were performed ten to fifteen minutes apart, one followed by the ECG ordered scan described herein and one by the conventional sequentially ordered cardiac gated scan. Their order was randomized for each participant. The scanning parameters for the sequentially ordered cardiac gated scan were identical (including trigger delay) except for the number of slices (reduced to 18-20) and the slice thickness (increased to 6 mm). This was done to obtain the same volumetric coverage within the same acceptable breath hold time (up to 21 seconds depending on heart rate.) While the scan time (e.g., 20 seconds) and volumetric coverage remained the same, the ECG ordered scan doubled the slice resolution. As a result, voxel size went from 2×2×6 for the conventional cardiac gated scan to 2×2×3 mm for the ECG ordered scan.

Figure 5A:
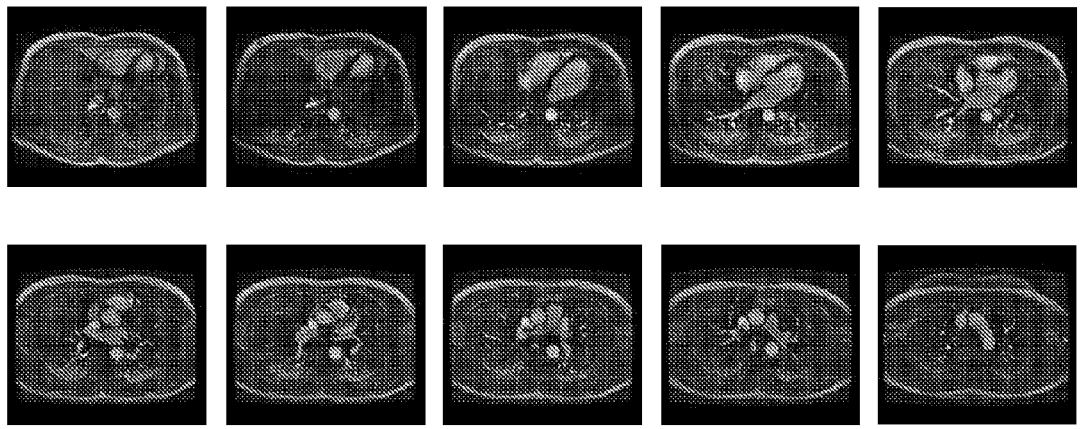
FIG. 5a is a series of source images from an ECG ordered contract enhanced MRA of a patient demonstrating the coverage of the whole heart, pulmonary arteries and veins and aortic root.
Figure 5B:
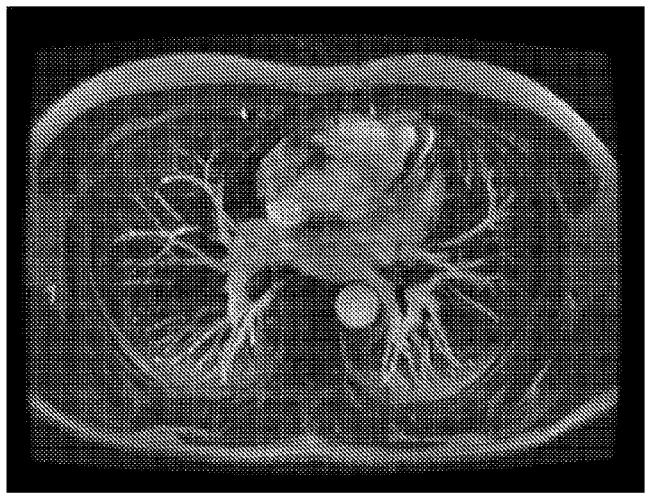
FIG. 5b is an axial image of the patient of FIG. 5a derived from reformatting the images of FIG. 5a allowing visualization of the LAD (left anterior descending coronary artery)
Figure 5C:
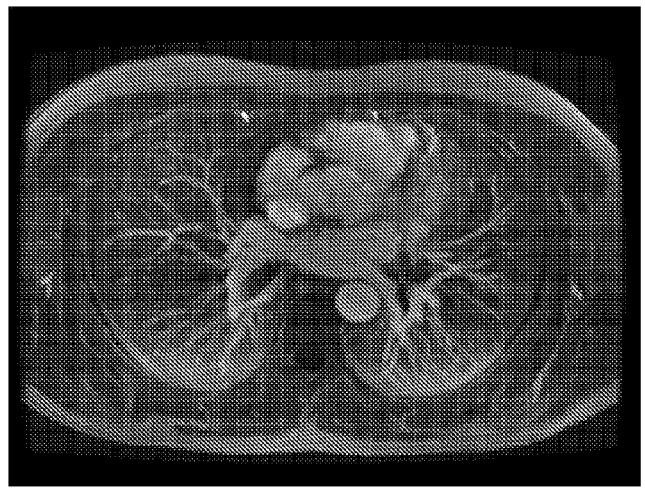
Figure 5D:
Figure 5E:
Figure 5F:
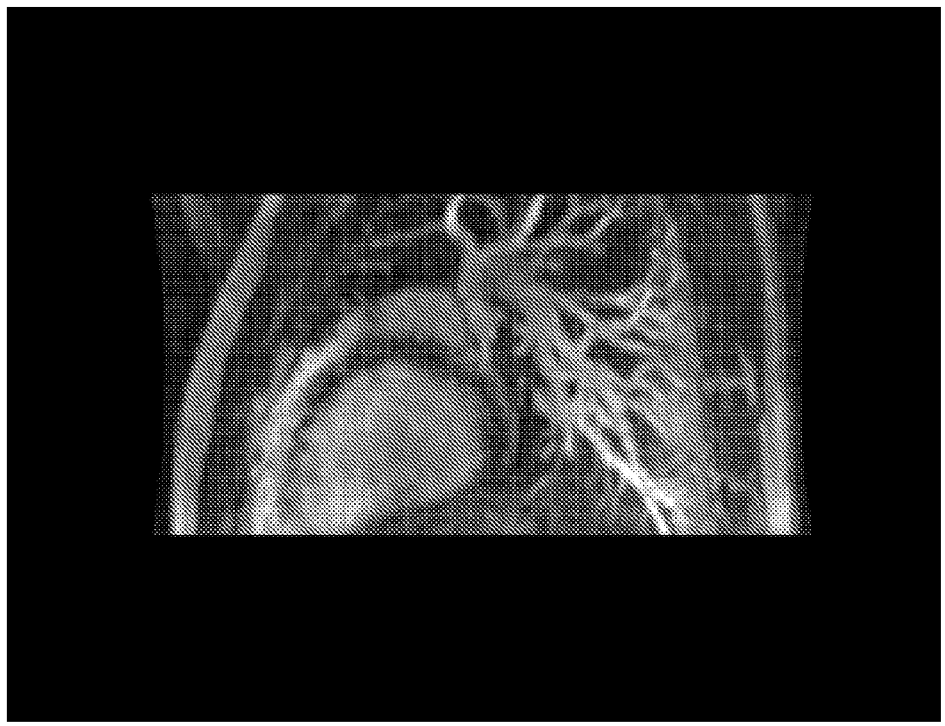
Figure 5G:
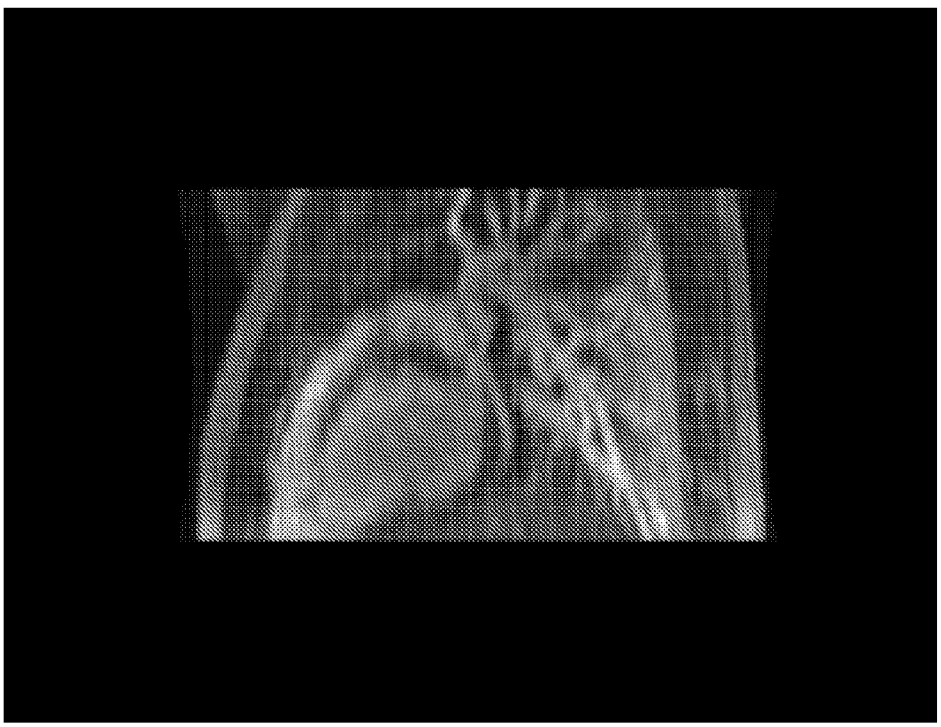

FIG. 5a shows source images from an ECG ordered contrast enhanced MRA of a male volunteer in accordance with the technique described above. Not all slices are shown. The images demonstrate the coverage of the whole heart, pulmonary arteries and vein and aortic root. A small slice thickness allows better reformatting of the axial images into arbitrary view planes. Inspection of the images shows that the images are free from the ghosting artifacts that are present in ungated scans caused by pulsation of the ascending aorta and motion of the heart. Reformatting of the image data allows visualization of the LAD (left anterior descending coronary artery) as shown in FIG. 5b (axial view), FIG. 5d (coronal view) and FIG. 5f (sagital view). Acquired voxel size was 2×2×3 mm reconstructed to 1×1×1.5 mm. Residual cardiac motion artifacts are visible within the cardiac chambers. FIG. 5c (axial view), FIG. 5e (coronal view), and FIG. 5g (sagital view) shows reformatted image data from a conventional sequentially ordered gated scan. Acquired voxel size was 2×2×6 mm reconstructed to 1×1×3 mm. It can be seen that the smaller slice thickness of the ECG ordering technique described above allows better reformatting of the axial images into arbitrary view planes as compared to the conventional sequentially ordered sequence.

Figures 6A, 6B:
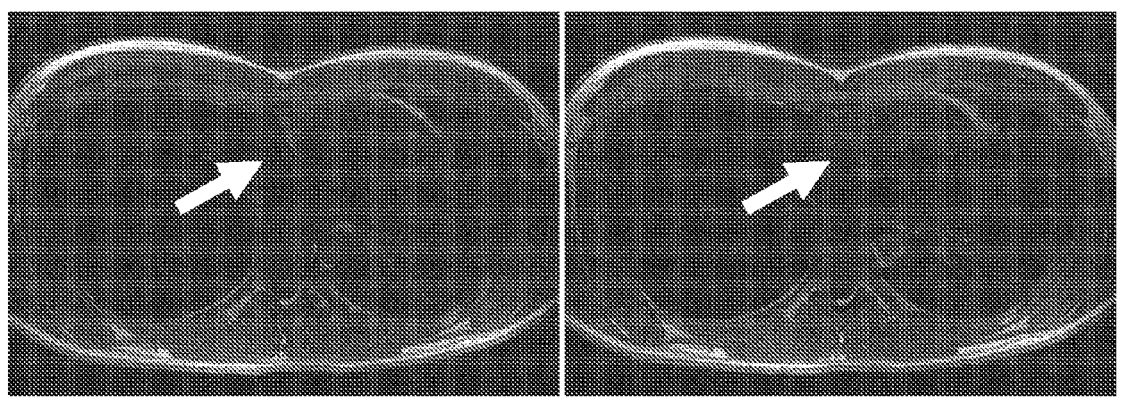
FIG. 6a is an image a slice of a right coronary artery (RCA) acquired from an ECG ordered sequence in accordance with the techniques described herein.
FIG. 6b is an image

FIG. 6a shows an ECG ordered sequence of a slice of a right coronary artery (RCA) in accordance with the techniques described herein. FIG. 6b shows a sequentially ordered gated sequence. The images demonstrate that the epicardial fat surrounding the RCA is seen well with the ECG ordering technique of FIG. 6a, but is heavily blurred in the sequentially ordered gated sequence of FIG. 6b.

From the foregoing, it can be seen that an ECG ordering technique for contrast enhanced thoracic magnetic resonance angiography has been described that combines the advantages of fast continuous scanning, recessed elliptical-centric view ordering and cardiac phase specific acquisition of the central part of k-space. The technique suppresses major ghosting and blurring artifacts caused by vascular pulsation and cardiac motion and does so without limiting the acquisition matrix or prolonging scan time and does not require additional navigator scans or scout scans.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An electrocardiogram (ECG) ordering method for acquiring data in a contrast enhanced magnetic resonance (MR) imaging or angiography, the method comprising:
    (a) at a processor, splitting a k-space view table into a central view table and a peripheral view table;
    (b) monitoring a cardiac cycle through ECG signal tracking; and
    (c) through a data acquisition system and the processor, acquiring views in the k-space view table throughout the cardiac cycle, including acquisition of views during at least two distinct phases of the cardiac cycle, wherein views in the central view table are acquired during rest periods of the cardiac cycle and views in the peripheral view table are acquired during non-rest periods of the cardiac cycle.

2. The ECG ordering method of claim 1 wherein views closest to the center of k-space are shifted to a position equal to $T_{REC} \times N_{RP}$, where $T_{REC}$ is the index of the heart beat in which the absolute center of k-space is to be acquired and $N_{RP}$ is the number of repetition times that fit in the rest period.

3. The ECG ordering method of claim 1 wherein the said splitting the k-space view table into the central view table and the peripheral view table includes splitting the k-space view table into the central view table with the central part of k-space equal to $N_{RP} \times N_{CI}$, where $N_{RP}$ is the number of repetition times that fit in the rest period and $N_{CI}$ is an expected number of cardiac intervals.

4. The ECG ordering method of claim 1 wherein the said acquiring views in the central view table during the rest periods comprises acquiring views in the central view table during mid-diastolic periods of the cardiac cycle.

5. The ECG ordering method of claim 1, the method further comprising:
    turning off ECG signal tracking and acquiring all remaining views if at least one of the following conditions occurs: when an ECG trigger is not detected for a predetermined length of time and when a sequence does not traverse a predetermined amount of views in the central view table.

6. The ECG ordering method of claim 5, wherein the predetermined length of time is measured by a number of cardiac cycles.

7. The ECG ordering method of claim 5, wherein the said all remaining views are acquired starting from a remaining view closest to the center of k-space and ending with the edge of k-space.

8. The method of claim 1, wherein views are acquired during both the diastole and systole of the cardiac cycle.

9. An electrocardiogram (ECG) ordering method for acquiring data in a contrast enhanced magnetic resonance imaging or angiography, the method comprising:
    (a) at a processor, splitting a k-space view table into a central view table and a peripheral view table;
    (b) monitoring a cardiac cycle through ECG signal tracking;

(c) at the processor, reordering the central view table according to a recessed elliptical centric view;
(d) through a data acquisition system and the processor, acquiring views in the k-space view table throughout the cardiac cycle, including acquiring views in the central view table during a rest period of the cardiac cycle and acquiring views in the peripheral view table during non-rest periods of the cardiac cycle, wherein views are acquired during at least two distinct phases of the cardiac cycle;
(e) at the processor, dividing the peripheral view table into a first section and a second section, wherein views from the first section are acquired before the rest period and views from the second section are acquired after the rest period;
(f) at the processor, further dividing the two sections of the peripheral view table into arches containing views that have a similar k-space radius, wherein an arch from the first section is traversed before the rest period and an arch from the second section is traversed after the rest period; and
(g) through the data acquisition system and the processor, determining whether all views in an arch have been completely acquired by searching for an unacquired view in the arch, and if all views in the arch have been acquired, searching for an unacquired view outside of the arch.

10. The ECG ordering method of claim 9, the method further comprising:
at the processor, adjusting at least one of the first section and the second section of the peripheral view table according to a prescribed trigger delay and heart rate.

11. The ECG ordering method of claim 9, wherein views in the k-space view tables are acquired continuously throughout a cardiac cycle.

12. The ECG ordering method of claim 9, wherein the said searching for an unacquired view outside of the arch further comprises:
searching for a view in an arch that is further away from the k-space center than the arch in which all views have been acquired.

13. The ECG ordering method of claim 9, the method furthering comprising:
through the data acquisition system and the processor, determining whether all views in the central view table have been completely acquired by searching for an unacquired view in central view table, and if all views in the central view table have been acquired, searching for an unacquired view outside of the central view table.

14. The ECG ordering method of claim 9, the method further comprising:
turning off ECG signal tracking and acquiring all remaining views if at least one of the following conditions occurs: when an ECG trigger is not detected for a predetermined length of time and when a sequence does not traverse a predetermined amount of views in the central view table.

15. The ECG ordering method of claim 14, wherein the predetermined length of time is measured by a number of cardiac cycles.

16. The ECG ordering method of claim 14, wherein the said all remaining views are acquired starting from a remaining view closest to the center of k-space and ending with the edge of k-space.

17. The method of claim 9, wherein views are acquired during both the diastole and systole of the cardiac cycle.

* * * * *